US006670609B2

(12) United States Patent
Franzen et al.

(10) Patent No.: US 6,670,609 B2
(45) Date of Patent: Dec. 30, 2003

(54) SAMPLE SUPPORT PLATES FOR MASS SPECTROMETRY WITH IONIZATION BY MATRIX-ASSISTED LASER DESORPTION

(75) Inventors: Jochen Franzen, Bremen (DE); Jens Rebettke, Schwanewede (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 10/222,764

(22) Filed: Aug. 16, 2002

(65) Prior Publication Data

US 2003/0057368 A1 Mar. 27, 2003

(30) Foreign Application Priority Data

Aug. 17, 2001 (DE) ........................................ 101 40 499

(51) Int. Cl.$^{7}$ ........................... H01J 49/00; B01D 9/44; C12Q 1/68; C12Q 1/37

(52) U.S. Cl. ............................. 250/288; 435/6; 435/23; 435/24; 435/287.2; 436/177; 536/24.3

(58) Field of Search ............................. 250/288; 435/6, 435/23, 24, 287.2; 436/177; 536/24.3

(56) References Cited

U.S. PATENT DOCUMENTS 5,770,860 A 6/1998 Franzen
6,225,061 B1 * 5/2001 Becker et al. ................. 435/6
6,287,872 B1 9/2001 Schürenberg et al.
6,383,742 B1 * 5/2002 Drmanac et al. .............. 435/6
6,485,913 B1 * 11/2002 Becker et al. ................. 435/6
2002/0005478 A1 * 1/2002 Hillenkamp et al. ........ 250/288
2002/0034737 A1 * 3/2002 Drmanac ....................... 435/6
2002/0042048 A1 * 4/2002 Drmanac ....................... 435/6
2003/0036084 A1 * 2/2003 Hauser et al. ................. 435/6
2003/0057368 A1 * 3/2003 Franzen et al. ............. 250/281
2003/0073623 A1 * 4/2003 Drmanac et al. ............. 514/12
2003/0108897 A1 * 6/2003 Drmanac ....................... 435/6

FOREIGN PATENT DOCUMENTS

GB 2 312 782 A 11/1997
GB 2 315 328 A 1/1998
GB 2378755 A * 2/2003 ............ H01J/49/04

OTHER PUBLICATIONS

Richmond et al., HGM2001 Poster Abstract: 5 new technologies, dated Jul. 1, 2001.*

Kitov et al., Letters to Nature vol. 403, Feb. 10, 2000, pp.669–672.*

Majors, R.E., Agilent technologies, "New Designs and Formats in Solid–Phase Extraction Sample Preparation", Dec. 2001.*

Lechner et al., "Large Scale Genotyping by Mass Spectroscopy: experience, advances and obstacles", Published Onine Dec. 19, 2001.*

* cited by examiner

*Primary Examiner*—John R. Lee
*Assistant Examiner*—Bernard Souw

(57) ABSTRACT

The invention concerns the structure of the sample support plates for mass spectrometric analysis of organic samples ionized by matrix-assisted laser desorption. The invention consists of a highly flat plate, electrically conductive at least on its surface, rigidly bonded to a base structure in such a way that together they form a body having the external dimensions of a microtitre plate, but such that thermal distortions of the surface cannot occur. The base structure may have both depressions for frictional gripping by a robot as well as a machine-readable identifier.

11 Claims, 1 Drawing Sheet

SAMPLE SUPPORT PLATES FOR MASS SPECTROMETRY WITH IONIZATION BY MATRIX-ASSISTED LASER DESORPTION

FIELD OF THE INVENTION

The invention concerns the structure of the sample support plates for mass spectrometric analysis of organic samples ionized by matrix-assisted laser desorption.

BACKGROUND OF THE INVENTION

The invention consists of a highly flat plate, electrically conductive at least on its surface, rigidly bonded to a base structure in such a way that together they form a body having the external dimensions of a microtitration plate, but such that thermal distortions of the surface cannot occur without bending the structure. The base structure may have both depressions for frictional gripping by a robot as well as a machine-readable identifier.

Mass spectrometry involving ionization by matrix-assisted laser desorption and ionization (MALDI) has become established as a standard procedure for the analysis of biomolecules. Time of flight mass spectrometers (TOF-MS) are used most frequently, although ion cyclotron resonance spectrometers (FT-ICR: Fourier transform ion cyclotron resonance) or high-frequency quadrupole ion trap mass spectrometers may also be used.

The biomolecules are usually located in an aqueous solution. In this context, the term biomolecules refers primarily to oligonucleotides (that is, genetic material in its various forms such as DNA or RNA) and proteins (the primary building blocks of living material), including their particular analogs and conjugates such as glycoproteins or lipoproteins.

The choice of the matrix substance for MALDI depends on the kind of biomolecule; well over a hundred different matrix substances have now become known. One of the tasks of the matrix substance is to hold the sample molecules, as well separated as possible, and to bind them to the surface of the sample support, to transfer them to the gas phase during the laser pulse by creating a vapor cloud, without destruction of the biomolecules and if possible without attachment of the matrix molecules, and finally, to ionize them through protonation or deprotonation. For this task, it has been found favorable for the analyte molecules to be incorporated in some way in the largely crystalline matrices as they crystallize on the surface of the sample support, or at least to be incorporated in the boundary surfaces between the small crystals that form during crystallization.

A range of different methods have become known for the application of the sample and the matrix. The simplest of these is application by pipetting a solution containing the sample and matrix onto a cleaned, metallic sample support. The droplet of solution creates a wetted area on the metal surface, whose size corresponds approximately to that of the diameter of the droplet and depends on how hydrophilic the metal surface is and on the properties of the droplet. After the solution has dried, a sample spot consisting of small matrix crystals is formed, having the size of the wetted area, although the quantity deposited over the wetted area is generally not evenly distributed.

For matrix substances that are either only slightly soluble in water, or not at all, such as -cyano-4-hydroxy-cinnamic acid, it has been found favorable to first create a very thin layer of crystals on the surface before applying the aqueous solution of analyte, for instance by applying a solution of the matrix substance in acetone.

An improved method of sample application has been described in German Patent No. DE 197 54 978 C1, in which the surface of the sample support is provided with extremely small, easily wetted (hydrophilic) anchor areas for the sample droplets, located on the desired grid of sample spots and surrounded by an environment that is not easily wetted (hydrophobic). The droplets containing the dissolved analyte molecules that are pipetted onto the surface attach themselves to these anchor regions and crystallize there much more evenly than they do without an anchor. The crystal conglomerates bind to the surface of the sample support in these hydrophilic anchor regions quite strongly.

A favorable method of sample application is known for oligonucleotides, but is restricted to use with silicon chips. The oligonucleotides bonded to the surface of the chips have microdroplets of matrix solution (3-HPA) containing only a few hundred picoliters shot at them by piezo-electrically driven micropipettes, resulting in a crystal structure with an evenly distributed sensitivity to the MALDI process.

All these procedures for the application and crystallization of the samples depend, however, very strongly on the properties of the surface, and in particular on the properties of the hydrophilic anchor surfaces. These properties include the chemical composition of the surface of the support, the degree to which the surface has been oxidized, and most particularly its smoothness. It is especially important that extreme surface cleanliness is achieved, because even the slightest traces of impurities can seriously affect the MALDI process. It is particularly important that no alkali ions emerge from the surface into the applied sample solution.

If time of flight mass spectrometers are used for the analysis, the surface of the sample support is also required to be extraordinarily flat. Undulations in the surface may not exceed a few tens of micrometers, otherwise the determination of the mass from the flight time is made more difficult.

Up until now it has been found that only a few types of sample support material are, at least to some degree, universally usable. These particularly include (1) smooth rolled stainless steel sheet, approximately 3 mm thick, with a highly shining surface; (2) glass plates onto which a conductive layer has been vaporized; (3) silicon wafers. The critical significance of the nature of the surface can be seen from the fact that, for instance, a milled stainless-steel surface is inferior to a rolled surface. For some types of sample, on the other hand, ground surfaces are favorable, although, once again, grinding a rolled surface is better than grinding a milled surface.

Previous experience has demonstrated that all the materials that are favorable to use have the form of more or less thin plates.

If sample support plates are to be handled automatically, it is favorable to retain the form of microtitre plates that has become an industry standard and use it for the sample support plates also. It is true that this industrial standard does not have an entirely unambiguous definition; a number of attempts at standardization have been made, and these differ from one another in details that are, however, not important here. The microtitre plate is significantly thicker than the favorable plate material described above. Only sample support plates having approximately the form of microtitre plates can be processed and handled by commercially available pipetting robots. Identifiers can be printed and read on the front face, usually a barcode. The plates can be picked up by standardized grippers, and the sample droplets can be applied to them with the aid of multi-pipette heads. They can be stacked in magazines or inserted in appropriate drawer-like storage containers. The underside of the microtitre plate functions, when they are stacked in magazines, as a relatively well sealed, at least dust-proof, cover for the plate beneath.

If the underside is made of a material that does not permit condensation of the matrix material, which continuously undergoes light evaporation, stacking the plates can permit a long storage capacity for plates that have had samples and matrix material applied to them.

The use of MALDI sample supports having the form of microtitre plates as a base onto which samples may be placed by multiple pipetting heads has already been described in German Patent No. DE 196 28 178 C2 (corresponding to British Patent No. GB 2 315 329 or U.S. Pat. No. 5,770,860).

The form of a microtitre plate can only be created by using an underlying base that must be bonded to the sample plate. Removable structures are already commercially available for sample supports in the form of plates. In accordance with the requirements of Good Laboratory Practice (GLP), observed nowadays in all certified laboratories, the sample supports must be provided with a permanently attached identification. Removable base structures can not, however, be given identifications in conformity with GLP.

The finished assembly of the sample support plates consisting of the sample plate and the base structure must be suitable for use in a vacuum, and must not release polluting substances, neither in the vacuum of the mass spectrometer nor in the washing baths, that could collect on the surface of the support and thus contaminate the sample or disturb the MALDI process. It is of particular importance that the surface of the sample supports do not bend or distort under the influence of temperature changes.

Base structures for the sample support plates can economically be made from injection molded metal or, particularly economically and favorably, from a vacuum-compatible plastic. A stainless steel sample support plate, however, exhibits a thermal expansion of $12\times10^{-6}$ $K^{-1}$. This coefficient of expansion is larger than that of any other metals or metal alloys, but significantly smaller than that of the plastics that can be used here. While there are, at the extreme, plastics with expansion rates that are this low, they do not satisfy the requirements for vacuum compatibility and washability.

As a stainless steel base structure is too expensive, and because pairs of materials with the same thermal expansion are not found, it is not possible to glue the sample plate and the base structure together, because thermal bending, as with a bimetallic strip, will always occur, which in this case would prevent their use in mass spectrometers. Adhesives, moreover, do not generally satisfy the requirement that they will not evolve gases or that impurities will not be released during washing.

Similar considerations also apply to sample support plates made of glass or silicon: here again, it is difficult to find pairs of materials with the same expansion coefficients. Known pairs that do have the same expansion coefficient, such as Kovar glass and Kovar metal, are expensive and difficult to machine.

SUMMARY OF THE INVENTION

The fundamental idea of the invention is to bond the sample plate and the base structure only at a small number of points—preferably at only three points—in such a way that while differences in the expansion of the sample plate and the base structure may indeed generate compressive or tensile forces in the plane of the plate, bending forces or twisting forces can nevertheless not be exerted on the sample plate.

This approach provides considerable freedom in relation to the selection of the material for the base structure. It is therefore possible to use an economical injection molding or an economically processed plastic that satisfies the requirements for washability and vacuum compatibility.

The sample plate and the base structure can, for instance, be rigidly joined together by means of three protrusions on the base structure pressed into holes in the sample plate, implemented in such a way that a small clearance remains between the sample plate and the base structure. Twisting or bending forces cannot be transferred through three protrusions. It is also, however, possible for metallic or non-metallic nails similar to rivets to be pressed through holes in the sample plate into recesses in the base structure. The rivet-like nails can have slightly conical heads that can only apply forces to the sample plate via a narrow contact rim, but cannot apply bending forces through full-faced pressure against the sides of the hole. The elastic or non-elastic flexibility of the rivet-like nails or the protrusions can even, to a limited extent, take up and balance shearing forces, so that only small tensile or compressive forces are generated in the sample plate, an arrangement that is particularly favorable for glass sample plates. Small raised support areas on the base structure around the connection points provide a clearance over a wide area between the sample plate and the base structure, so that twisting or bending of the base structure is not transmitted to the sample plate.

The base structure can have the form of a frame, or have the full area of a plate. Using a full plate as the base structure can, through the shape of the underside structure, in turn serve as a good cover for a sample support situated beneath it. The base structure can be provided with an inseparable barcode or with a transponder that gives the identity of the sample support in conformity with GLP. A transponder can even contain an occupancy status and a history of use. The base structure can, at its edge, also be provided with special holes or grooves to facilitate reliable gripping by robots. Grooves to assist insertion into the vacuum system of the mass spectrometer can also be provided here.

This allows the sample plate to have precisely the same area as a microtitre plate, although it can also be smaller, in which case the base structure can supply the missing edge with sufficient play. It is even possible to use divided sample plates, each having smaller dimensions. In particular, the sample plate can carry a pattern of hydrophilic anchors in a hydrophobic environment.

DETAILED DESCRIPTION

Figure 1:
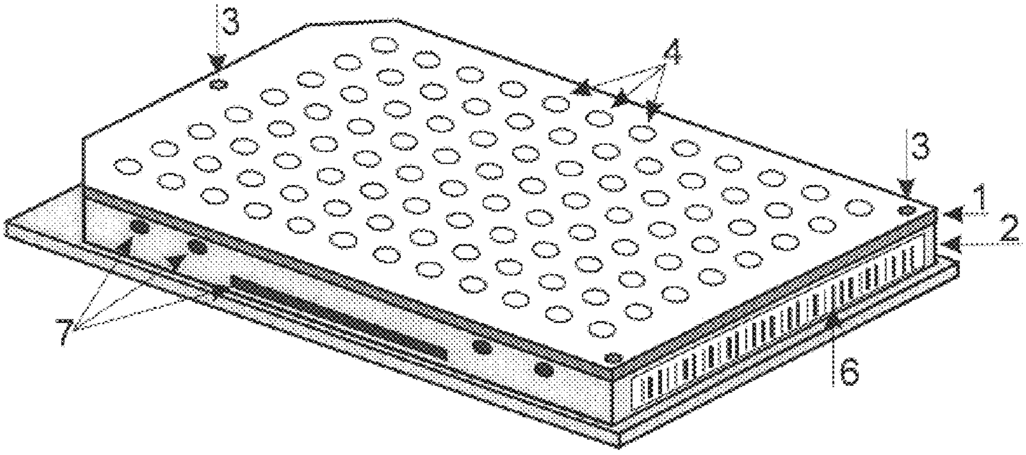
FIG. 1 shows a sample support that accords with this invention. A stainless steel sample plate (1) is fastened to a plastic base structure (2), whereby protrusions on the base structure (2) that are not visible are pressed into the holes (3) of the sample plate. Rings (4) are cut in to the surface of the sample plate (1) in order to prevent the sample droplets from spreading during application. The base structure (2) has a barcode (6) on its front, and has depressions (7) to allow it to be gripped by certain gripping tools. In this case there are four pairs of round depressions and one pair of grooves.
Figure 2:
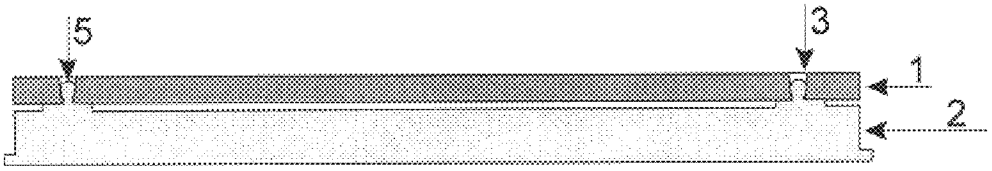
FIG. 2 shows a cross section through the attachment plane of the sample support shown in FIG. 1 with the stainless steel sample plate (1), the plastic base structure (2) and the holes (3), where protrusions in the form of lobes (5) with relatively narrow necks are firmly pressed into the slightly conical holes (3).
Figure 3:
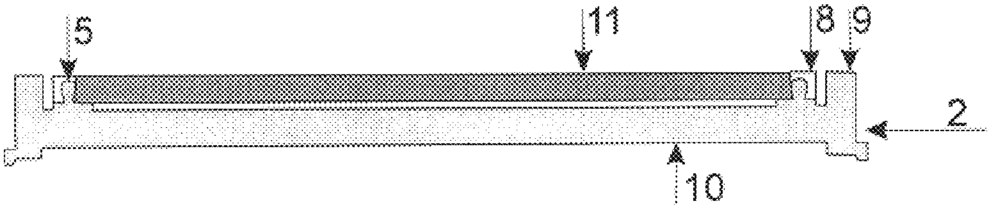
FIG. 3 shows a glass sample plate (11), into the side of which grooves (8) are ground instead of the holes to accept the protrusions (5) of the base structure. The glass sample plate (11) is smaller than a microtitre plate, and is protectively surrounded by a border (9) of the plastic base structure (2). The floor of the base structure (2) has a stepped design (10) to serve as a cover for the plate below.

A particularly favorable embodiment of a sample support (1) with a stainless-steel surface consists of a smooth-rolled stainless-steel sample plate approximately 3 mm thick, given the outline form of a microtitre plate by stress-free waterjet cutting, and provided near its edge with three slightly conical holes (3) together with a base structure (2) of plastic having three protrusions (5) that can be pressed into the holes. The protrusions have a somewhat thinner neck, and can be forcibly pushed into the holes in the sample plate, the holes being somewhat narrower on the underside. If the protrusions consist of thermoplastic material, then it is also possible for the upper part of the protrusions in the holes to be adapted to the shape of the hole through heat deformation, similar to riveting, by means of a hot punch.

When heated from 20° Celsius to about 60° Celsius in a washing bath, protrusions that are 100 millimeters apart will separate, if the coefficient of expansion is $30\times10^{-6}$ $K^{-1}$, by 0.12 millimeter, whereas the spacing between the holes in the stainless steel plate will only increase by about 0.04 millimeter. The difference of 0.08 millimeter can be accommodated by elastic bending of the necks of the protrusions.

Similar considerations apply to sample supports (11) made of glass. In this case, the difference in expansion is about 0.1 millimeter, and this can again be accommodated by the flexibility of the protrusions. It is helpful in this case for the protrusions (5) to have a separation at room temperature that is smaller than that of the holes in the glass, so that some compressive stress is always retained in the glass, thus ensuring that even at relatively high washing temperatures tensile forces that could cause the glass to crack will not arise. It is also helpful to keep the surface area of glass plates (11) smaller than the surface of a microtitre plate and to allow a plastic border (9) of the base structure to stand around the glass plate, as protection for the edges of the glass plate. In such glass plates (11), smaller than the area of microtitre plates and embedded in them, it is also possible for the holes (3) to be replaced by groove-like notches (8) in the edges of the glass plates; tensile forces are then no longer possible at all. Conductive layers can be evaporated on to the glass plates in a number of different ways; vapor deposition with cesium iodide has been found to be very favorable.

It is helpful for all kinds of sample plate to provide the plastic base structure with a support area raised approximately 0.3 millimeter and having a diameter of about 5 millimeters around the protrusions, to give the sample plate a defined support area and to create a small clearance between the sample plate and the base structure.

The surface of the stainless-steel sample supports (1) can be given special markings to accept the samples. In particular, lightly milled ring-shaped markings (4) with a diameter of approximately 2 millimeters have been found to be favorable, because these prevent the sample droplets from freely running away during application. It is possible here to use the conventional quadratic grid of microtitre plates, in other words 96 sample rings 9 millimeters apart, 384 sample rings each 4.5 millimeters apart, 864 sample rings 3 millimeters apart or 1536 sample rings at a spacing of 2.25 millimeters. The usual X-Y identifiers for the sample locations can also be provided at the edge of the sample plate.

Hydrophilic anchor areas to hold the droplets in an otherwise hydrophobic sample support surface, as described in German Patent No. DE 197 54 978 C2, have been found to be particularly favorable. Here the term "hydrophobic" surface means a surface that is not easily wetted and that has little affinity for the liquid used for the samples, even when this (exceptionally) is not an aqueous solution. In the case of an oily sample solution, therefore, the surface should correspondingly be lipophobic. Generally, however, the biomolecules dissolve most effectively in water, sometimes with the addition of organic, water-soluble solvents. In the same way, a "hydrophilic" surface means a surface that is easily wetted by the type of sample liquid being used, even if this is not an aqueous solution.

The markings can be printed onto glass sample plates (11).

Because of the fixed connection between the sample plate and the base structure, identifiers can be applied to the base structure in conformity with GLP. The standard for microtitre plates specifies a barcode (6) on the front of the microtitre plate. This barcode (6) can also be applied to the base structure. The barcode (6) then provides a unique identification for the sample support. The barcode can also be read in the mass spectrometer, providing an unambiguous assignment of the sample being measured to the results of the analytic procedure.

A transponder is an intelligent solution for plate identification. The transponder code can be divided into a non-erasable section and a rewritable section. The non-erasable section can contain a unique identifier for the identity of the sample support. It can, furthermore, contain information about unalterable properties of the sample support, such as an identifier for a "stainless-steel sample support with 1536 hydrophilic anchors" or a "silicon wafer sample support with 6144 etched hollows". These identifiers can, for instance, be read by the pipetting station, and also used to reject an unsuitable sample support. The alterable part of the code can contain information about the type of washing and the occupancy with samples, a counter for the number of times that the sample support has been used before, a code for special types of analysis for which this sample support is reserved, a code for support-specific corrections such as the positions on the support, or similar information.

Gripper holes and gripper grooves (7) can be provided on the long sides of the sample supports, making it possible for special grippers to hold the support. A sample support must not be dropped by a gripper. One reason is that dropping a support would halt automatic operation, and a further reason is that a plate occupied by valuable samples can cost a fortune, for example if preparation of the samples required a whole year's teamwork, or may even be irreplaceable.

The underside (10) of the base structure can favorably serve as a cover for the support plate stacked underneath it.

The fastening between the sample plate (1) and the base structure (2) does not, however, have to be created by protrusions (5) that are part of the base structure (2). Pins of metal or plastic with thickened heads can also be pressed through the holes (3) in the sample plate (1) into appropriately formed channels in the base structure (2). The heads can, for instance, be round or conical. The channels are open to the underside, so that they can be properly evacuated.

What is claimed is:

1. Sample support for the mass spectrometric analysis of samples with ionization by matrix-assisted laser desorption, consisting of a flat sample plate to take the samples and a base structure, together creating the external form of a microtitre plate wherein the sample plate has holes or grooves, and the base structure is rigidly bonded to the sample plate by pins or protrusions anchored into the holes or grooves.

2. Sample support according to claim 1 wherein there are three such bonding points, and the base structure is attached with a small clearance from the sample plate.

3. Sample support according to claim 2 wherein the base structure has slightly raised supporting surfaces surrounding the bonding points to take the sample plate, and these raised surfaces determine the clearance.

4. Sample support according to claim 1 wherein the protrusions or pins are so flexible that they can absorb part of the shear forces generated as a result of the different rates of expansion of the sample plate and the base structure when temperature changes occur, without fully transferring these forces to the sample plate.

5. Sample support according to claim 1 wherein the sample plate consists of stainless steel, glass onto which a conductive layer has been evaporated, or silicon.

6. Sample support according to claim 1 wherein the base structure consists of an injection molding or of vacuum-compatible plastic.

7. Sample support according to claim 1 wherein the base structure carries a machine-readable identifier.

8. Sample support according to claim 7 wherein the identifier is a barcode.

9. Sample support according to claim 7 wherein the identifier is a transponder.

10. Sample support according to claim 9 wherein the identifier in the transponder contains a non-alterable partial code that identifies the sample support, and a partial code that can contain the current occupancy of the sample support, specific current properties of the sample support, data on the history of its occupancy and/or the frequency of its usage.

11. Sample support according to claim 1 wherein the base structure has holes or grooves at the side to facilitate frictional gripping by a gripper robot.

* * * * *